United States Patent [19]

Usui et al.

[11] Patent Number: 5,177,013
[45] Date of Patent: Jan. 5, 1993

[54] PREPARATION OF AN IMMOBILIZED LIPASE HAVING A LOW WATER CONTENT WITHOUT DRYING

[75] Inventors: Naoki Usui; Naoto Kato; Tsuyoshi Nakamatsu; Jun Kurashige, all of Kawasaki, Japan

[73] Assignee: Ajinomoto Co., Inc., Tokyo, Japan

[21] Appl. No.: 554,853

[22] Filed: Jul. 20, 1990

[30] Foreign Application Priority Data

Jul. 31, 1989 [JP] Japan ................. 1-198474

[51] Int. Cl.⁵ .............. C12N 11/14; C12N 9/20; C12N 11/02; C12N 11/08
[52] U.S. Cl. ..................... 435/176; 435/134; 435/177; 435/178; 435/180; 435/187; 435/198
[58] Field of Search .............. 435/134, 174, 176, 177, 435/178, 180, 187, 198

[56] References Cited

U.S. PATENT DOCUMENTS

| | | | |
|---|---|---|---|
| 4,416,991 | 11/1983 | Matsuo et al. | 435/134 |
| 4,472,503 | 9/1984 | Matsuo et al. | 435/174 |
| 4,798,793 | 1/1989 | Eigtved | 435/134 |
| 4,818,695 | 4/1989 | Eigtved | 435/134 |
| 5,061,498 | 10/1991 | Matsuzaki et al. | 435/134 X |

FOREIGN PATENT DOCUMENTS

| | | |
|---|---|---|
| 0320132 | 6/1989 | European Pat. Off. |
| 60-98984 | 9/1983 | Japan . |
| 61-202688 | 9/1986 | Japan . |
| 62-134090 | 6/1987 | Japan . |
| 63-22795 | 5/1988 | Japan . |
| 63-214184 | 9/1988 | Japan . |
| 1153090 | 6/1989 | Japan . |
| 1153097 | 6/1989 | Japan . |

*Primary Examiner*—David M. Naff
*Attorney, Agent, or Firm*—Oblon, Spivak, McClelland, Maier & Neustadt

[57] ABSTRACT

Lipase is absorbed on a carrier to provide an immobilized lipase preparation containing 0.5 to 8% water by a process that does not require drying. The process is carried out by providing a solution or dispersion of lipase in a liquid solvent, mixing the solution or dispersion of lipase with a carrier to provide a mixture containing 0.5 to 8% water and kneading the mixture to produce the immobilized lipase preparation. The solution or dispersion of lipase may contain an enzyme activity enhancing agent such as a fatty acid or its derivative such as lecithin. By not drying, an immobilized lipase preparation having higher activity is obtained.

21 Claims, No Drawings

5,177,013

PREPARATION OF AN IMMOBILIZED LIPASE HAVING A LOW WATER CONTENT WITHOUT DRYING

BACKGROUND OF THE INVENTION

This invention relates to a process of preparing an immobilized lipase preparation useful for modification of fats and oils.

There have been known processes of modification of fats and oils using an enzyme preparation which comprises a lipase absorbed on a carrier. Since water inhibits the modification reaction, it is desirable that water content is as low as possible not only in the reaction system but also in the lipase preparation. So far such lipase preparation has been prepared by a process wherein a lipase solution is brought into contact with a carrier to be absorbed thereon and then dried for a long period of time under mild conditions. Such a process is not appropriate for economical modification of fats and oils in an industrial scale.

SUMMARY OF THE INVENTION

An object of the present invention is to provide a simple and economical process of preparing of an immobilized lipase preparation useful for modification of fats and oils.

The object has been accomplished by a process of preparing an immobilized lipase preparation wherein the lipase is absorbed on a carrier, comprising the steps of:

(a) providing a solution or dispersion of the lipase, and (b) mixing the solution or dispersion with the carrier whereby the lipase is absorbed and immobilized on the carrier, wherein the amount of water contained in the solution or dispersion and the carrier is 0.5 to 8% by weight based on the dry weight of the carrier.

DETAILED DESCRIPTION OF THE INVENTION

The lipase and the carrier used in the present invention are those conventionally used. Examples of the lipase include those derived from plant seeds such as castor-oil seeds or rapeseeds, molds, yeasts and bacteria, and conveniently freeze-dried lipase which is commercially available and has high hydrolytic activity.

Examples of the carrier used in the present invention include inorganic ones such as Celite, pig bone, diatomaceous earth, kaolinite and calcium carbonate; or organic ones such as weakly or strongly acidic cation exchange resins, weakly or strongly basic anion exchange resins and synthetic adsorbents. Ion exchange resins having high water absorption are particularly preferred.

The solution or dispersion of the lipase may be prepared by providing 0.001 to 0.2 part by weight of the lipase and optionally 0.0001 to 0.2 part by weight of an enzyme activity enhancing agent based on one part by weight of the carrier, adding an appropriate amount of a solvent and mixing them.

As an enzyme activity enhancing agent, there may be used a basic polysaccharide such as chitin, chitosan and water-soluble chitin; a fatty acid derivative such as a phospholipid such as lecithin, mono-, di- and tri-glycerides, for example, fats and oils such as rapeseed oil, sesame oil, soybean oil, olive oil, safflower oil, corn oil, palm oil, peanut oil, sunflower oil, sardine oil and herring oil; and a fatty acid such as oleic acid, α-linolenic acid, γ-linolenic acid, stearic acid and palmitic acid.

In the present invention, it is preferable that the lipase solution or dispersion contains at least one of the enzyme activity enhancing agent, preferably a combination of at least one of basic polysacchrides and at least one of fatty acids or derivatives thereof. Particularly preferred are lecithin, chitin, chitosan and water-soluble chitin, most preferably a combination of lecithin and at least one of chitin, chitosan and water-soluble chitin.

The amount of such an activity enhancing agent used usually is at least 1%, preferably at least 5% by weight based on the weight of the lipase. The upper limit of the amount is not critical. However, it becomes difficult to knead the lipase solution or dispersion because of its high viscosity if the amount of chitin, chitosan or water-soluble chitin exceeds 50% by weight.

As a solvent, there may be used, in addition to water, alcohol, acetone, glycerol, fats and oils, hexane, surfactant, or mixtures thereof in order to disperse the lipase and the enzyme activity enhancing agent optionally used into water.

The lipase preparation may be prepared by adding the lipase solution or dispersion to the carrier and kneading the mixture sufficiently. The water content of the carrier is previously adjusted so that the total water content in the carrier and the lipase solution or dispersion is 0.5 to 8% by weight based on the dry weight of the carrier. If the total water content is less than 0.5% by weight, lipase activity is not fully revealed. If it exceeds 8% by weight, the lipase preparation must be dried before use, which means that the object of the present invention is not achieved. Kneading may be made by conventional mechanical mixing apparatus such as a kneader. It is possible to prepare a large amount of the lipase preparation in a very short time.

During the addition of the lipase solution or dispersion to the carrier and kneading, it is preferable to maintain the mixture at temperature of −10° to 50° C. However, the components can be added and kneaded even at a temperature higher than 50° C. to prepare a lipase preparation having high enzyme activity because the addition and the kneading can be conducted in a very short time during which the enzyme is hardly inactivated.

In conventional processes of preparing enzyme preparations, a large amount of water is used to prepare a lipase solution or dispersion. In order to remove excess water from the enzyme preparation after the enzyme is adsorbed on a carrier, it is necessary to dry the preparation under mild conditions at 30° to 50° C., at 0.01 to 100 Torr for a long period of time so that the enzyme is not inactivated.

In contrast, the process of preparing a lipase preparation of the present invention does not require such a drying step which would inactivate lipase activity so that it is possible to prepare a lipase preparation having higher enzyme activity.

The lipase preparation of the present invention can be used advantageously for modification of vegetable oils such as sesame oil, rapeseed oil, cottonseed oil, soybean oil, camellia oil, olive oil, castor oil, coconut oil and palm oil; fish or sea animal oils such as sardine oil, herring oil, saury oil, shark oil and whale oil; land animal oils such as tallow and lard; and mixtures thereof.

The lipase preparation prepared by the process of the present invention shows higher specific activity in modification reaction of fats and oils as defined below than lipase preparations prepared by conventional processes comprising a drying step.

Modification Reaction of Fats and Oils

Substrate: rapeseed oil/palm olein oil = 50/50 (w/w)
water content = less than 100 ppm
Reaction temperature: 60° C.

The substrate (10 g) and a lipase preparation (0.75 g) are mixed and shaked at 250 rpm.

$$\text{Specific activity (g/h/g)} = \frac{\Delta TG(g)}{\text{Time(h)} \cdot \text{Lipase(g)}}$$

$\Delta TG(g)$ = Change in the amount of triglyceride having 55 carbon atoms

EXAMPLES

The present invention will be explained more in detail with reference to the following nonlimitative examples.

Example 1

The enzyme used in this Example was freeze-dried lipase product derived from *Rhizopus delemar* (available from Amano Pharmaceutical, Lot A having hydrolytic activity of 3000 U/mg).

Water (25 g) was added to the above lipase product (13.3 g) and stirred sufficiently. The mixture was kneaded with 500 g of a cation exchange resin (WK-13 (a trade name) available from Mitsubishi Chemical Industries, Ltd.: water content = 2% by weight) to prepare a lipase preparation which contained 6.5% by weight of water and showed a specific activity of 2.8 g/h/g measured by the above method.

Comparative Example 1

According to the conventional vacuum drying method, a lipase preparation was prepared.

The lipase product (13.3 g) used in Example 1 were added to 1500 ml of water and stirred sufficiently. To the mixture, 500 g of WK-13 used in Example 1 was added and mixed. The mixture was then dried at 30° C. at a pressure of less than 10 Torr. The lipase preparation thus prepared contained 6.5% by weight of water and showed a specific activity of 1.2 g/h/g measured by the above method.

Example 2

Lecithin (4 g) and water (25 g) were fully mixed. The lipase product (13.3 g) used in Example 1 was added to the mixture and stirred sufficiently. The mixture was kneaded with 500 g of WK-13 used in Example 1 to prepare a lipase preparation which contained 6.5% by weight of water and showed a specific activity of 25 g/h/g measured by the above method.

Comparative Example 2

According to the conventional vacuum drying method, a lipase preparation was prepared.

Lecithin (4 g) and the lipase product (13.3 g) used in Example 1 were added to 1500 ml of water and stirred sufficiently. To the mixture, 500 g of WK-13 used in Example 1 was added and mixed. The mixture was then dried at 30° C. at a pressure of less than 10 Torr. The lipase preparation thus prepared contained 6.4% by weight of water and showed a specific activity of 17 g/h/g measured by the above method.

Comparative Example 3

According to the conventional freeze-drying method, a lipase preparation was prepared.

Lecithin (4 g) and the lipase product (13.3 g) used in Example 1 were added to 500 ml of water and stirred sufficiently. To the mixture, 500 g of WK-13 used in Example 1 was added and mixed. The mixture was then freeze-dried at −20° C. at a pressure of 0.5 to 2 Torr. The lipase preparation thus prepared contained 6.3% by weight of water and showed a specific activity of 18 g/h/g measured by the above method.

Example 3

Lecithin (4 g) and water (15 g) were fully mixed. The lipase product used in Example 1 (13.3 g) was added to the mixture and stirred sufficiently. The mixture was kneaded with 500 g of a synthetic adsorbent (HP-20 (a trade name) available from Mitsubishi Chemical Industries, Ltd.: water content = less than 1% by weight) to prepare a lipase preparation which contained 3.2% by weight of water and showed a specific activity of 17 g/h/g measured by the above method.

Comparative Example 4

According to the conventional vacuum drying method, a lipase preparation was prepared.

Lecithin (4 g) and the lipase product (13.3 g) used in Example 1 were added to 1500 ml of water and stirred sufficiently. To the mixture, 500 g of HP-20 used in Example 3 was added and mixed. The mixture was then dried at 30° C. at a pressure of less than 10 Torr. The lipase preparation thus prepared contained 3.1% by weight of water and showed a specific activity of 14 g/h/g measured by the above method.

Example 4

The same procedures of Example 2 were repeated except that the amount of water used for preparing a lipase solution or dispersion was changed to 25 g, 30 g, 35 g or 40 g to prepare a lipase preparation. Seemingly, the higher the water amount, the lower the yield of triglyceride in fats and oils reacted but the preparations showed a specific activity of 23, 24, 24 or 24 g/h/g, respectively.

Comparative Example 5

The same procedures of Example 4 were repeated except that the amount of water used for preparing a lipase solution or dispersion was changed to 45 g to prepare a lipase preparation which was not dispersed well in fats and oils when a specific activity was measured because water was too excessive.

Example 5

The same procedures of Example 2 were repeated except that 25 g of water used for preparing a lipase solution or dispersion was replaced by a mixture of water (15 g) and oleic acid (10 g), water (10 g) and oleic acid (15 g), or water (5 g) and oleic acid (20 g) to prepare lipase preparations which showed a specific activity of 22, 7 and 1 g/h/g, respectively. The lipase preparation prepared in the same manner as in Example 2 showed a specific activity of 24 g/h/g.

Example 6

The lipase preparation prepared in Example 2 was used for a continuous modification of fats and oils in a column.

The fats and oils used was a mixture of rapeseed oil and crude palm olein oil (50/50 (w/w)) which had been subjected to vacuum drying at 80° C. and at a pressure of less than 10 Torr for 20 minutes and contained less than 100 ppm of water. The lipase preparation (3 g) was charged in the column having an internal diameter of 1 cm and a length of 10 cm. The mixed fats and oils were passed through the column at a rate of 3.3 g/h. The reaction was carried out at 60° C. A half-life period of lipase activity was 430 hours.

Example 7

The enzyme used in this Example was freeze-dried lipase derived from Rhizopus delemar (available from Amano Pharmaceutical, Lot B having hydrolytic activity of 2700 U/mg).

Water (25 g) was added to the above lipase product (13.3 g) and stirred sufficiently. To the mixture, various sugars were added in the amount of 10% by weight based on the weight of the lipase product and then, the mixture was kneaded with 500 g of WK-13 used in Example 1 to prepare lipase preparations which contained 6.5 to 7.0% by weight of water.

A specific activity of the lipase preparations was measured by the above method. The results are shown in Table 1.

TABLE 1

| Sugar added | Activity (g/h/g) |
| --- | --- |
| None | 1.5 |
| Glucose | 1.4 |
| Glucosamine | 0.9 |
| N-acetylglucosamine | 1.5 |
| Dextrin | 1.1 |
| Chitin | 3.0 |
| Chitosan | 3.0 |
| Water-soluble chitin | 2.9 |

Example 8

Lecithin (4 g) and water (25 g) were fully mixed. The lipase product (13.3 g) used in Example 7 was added to the mixture and stirred sufficiently. To the mixture, various sugars were added in the amount of 10% by weight and then, the mixture was kneaded with 500 g of WK-13 used in Example 1 to prepare lipase preparations which contained 6.5 to 7.0% by weight of water.

A specific activity of the lipase preparations was measured by the above method. The results are shown in Table 2.

TABLE 2

| Sugar added | Activity (g/h/g) | Sugar added | Activity (g/h/g) |
| --- | --- | --- | --- |
| None | 15.5 | Dextran | 10.5 |
| Glucose | 14.3 | Na dextran sulfate | 14.3 |
| Glucosamine | 10.3 | CMC | 9.5 |
| Galactosamine | 10.3 | Alginic acid | 10.3 |
| N-acetylglucosamine | 16.5 | Curdlan | 11.5 |
| Erythritol | 17.8 | Chitin | 19.5 |
| Arabitol | 17.8 | Chitosan | 23.5 |
| Dextrin | 11.3 | Water-soluble chitin | 23.3 |

CMC: Carboxymethylcellulose
Degree of deacetylation of the water-soluble chitin was 40 to 60%.

Example 9

The procedures of Example 8 were repeated except that the amount of chitosan was changed as shown in Table 3. The addition of chitosan in the amount of 5% or more increases remarkably an enzyme activity as seen from the table.

TABLE 3

| Amount added (% by weight) | Specific activity (g/h/g) |
| --- | --- |
| 0 | 15.8 |
| 5 | 19.3 |
| 10 | 22.8 |
| 20 | 24.0 |
| 35 | 24.0 |
| 50 | 25.0 |

Example 10

The procedures of Example 8 were repeated except that the carrier, WK-13 was changed to HP-20. Chitosan and water-soluble chitosan increase remarkably an enzyme activity as seen from Table 4.

TABLE 4

| Compound (Amount added) | Specific activity (g/h/g) |
| --- | --- |
| None | 14.8 |
| Chitosan (10%) | 15.0 |
| Chitosan (35%) | 17.0 |
| Water-soluble chitosan (10%) | 18.0 |

Example 11

Water (25 g) was added to an activity enhancing agent and was fully mixed. The lipase product (13.3 g) used in Example 7 was added to the mixture and stirred sufficiently. The mixture was kneaded with 500 g of WK-13 used in Example 1 to prepare a lipase preparation which contained 6.3 to 6.6% by weight of water and showed the following specific activity measured by the above method.

TABLE 5

| Compound (Amount added) | | Specific activity (g/h/g) |
| --- | --- | --- |
| None | | 1.5 |
| Oleic acid | (50 g) | 7.5 |
| Oleic acid | (100 g) | 10.9 |
| Rapeseed oil | (50 g) | 4.0 |
| Rapeseed oil | (100 g) | 7.4 |
| Lecithin | (4 g) | 15.0 |
| Lecithin (4 g) + Oleic acid | (50 g) | 20.4 |
| Lecithin (4 g) + Oleic acid | (100 g) | 22.3 |
| Lecithin (4 g) + Rapeseed oil | (50 g) | 16.6 |
| Lecithin (4 g) + Rapeseed oil | (100 g) | 17.5 |

Example 12

An enzyme activity enhancing agent and water (25 g) were fully mixed. The lipase product (13.3 g) used in Example 7 was added to the mixture and stirred sufficiently. The mixture was kneaded with 500 g of WK-13 used in Example 1 to prepare lipase preparations which contained 6.5 to 7.0% by weight of water.

A specific activity of the lipase preparations was measured by the above method. The results are shown in Table 6.

TABLE 6

| Compound (Amount added) | | Specific activity (g/h/g) |
| --- | --- | --- |
| Oleic acid 50 g and chitin | 1.3 g | 9.1 |
| Oleic acid 50 g and chitosan | 1.3 g | 8.8 |

TABLE 6-continued

| Compound (Amount added) | | Specific activity (g/h/g) |
|---|---|---|
| Oleic acid 50 g and water-soluble chitin | 1.3 g | 9.7 |
| Chitin | 1.3 g | 3.0 |
| Chitosan | 1.3 g | 3.0 |
| Water-soluble chitin | 1.3 g | 2.9 |
| Oleic acid 50 g | | 7.5 |

The process of the present invention does not require the drying step after the lipase is absorbed on a carrier and therefore it makes it possible to prepare easily a lipase preparation without causing inactivation of the lipase.

What is claimed is:

1. A process of preparing an immobilized lipase preparation having a final water content of 0.5 to 8% without drying wherein the lipase is absorbed on a carrier, consisting essentially of the steps of:
   (A) providing a solution or dispersion of lipase in a liquid solvent; and
   (B) mixing the solution or dispersion of lipase with a carrier to provide a mixture containing 0.5 to 8% water and kneading the mixture to produce said immobilized lipase preparation.

2. The process of claim 1, wherein the lipase solution or dispersion contains an enzyme activity enhancing agent.

3. The process of claim 2, wherein the enzyme activity enhancing agent is a basic polysaccharide.

4. The process of claim 2, wherein the enzyme activity enhancing agent is a fatty acid or its derivative.

5. The process of claim 2, wherein the enzyme activity enhancing agent is a combination of at least one basic polysaccharide and at least one fatty acid or its derivative.

6. The process of claim 3, wherein the basic polysaccharide is selected from the group consisting of chitin and chitosan.

7. The process of claim 6, wherein the chitin is a water-soluble chitin.

8. The process of claim 4, wherein a fatty acid derivative is the enzyme activity enhancing agent and the fatty acid derivative is lecithin.

9. The process of claim 1, wherein the lipase is derived from a substance selected from the group consisting of plant seeds, molds, yeasts and bacteria.

10. The process of claim 1, wherein the lipase is derived from *Rhizopus delemar*.

11. The process of claim 1, wherein the carrier is selected from the group consisting of Celite, pig bone, diatomaceous earth, kaolinite calcium carbonate, weakly or strongly acidic cation exchange resins and weakly or strongly basic anion exchange resins.

12. The process of claim 1, wherein the carrier is selected from the group consisting of weakly or strongly acidic cation exchange resins and weakly or strongly basic anion exchange resins.

13. The process of claim 2, wherein the solution or dispersion of the lipase is prepared by providing 0.001 to 0.2 parts by weight of the lipase and 0.0001 to 0.2 parts by weight of an enzyme activity enhancing agent based on one part by weight of the carrier, adding an appropriate amount of a solvent to said lipase and said enzyme activity enhancing agent, and mixing.

14. The process of claim 13, wherein the enzyme activity enhancing agent is selected from the group consisting of chitin and chitosan.

15. The process of claim 14, wherein said chitin is a water-soluble chitin.

16. The process of claim 13, wherein the enzyme activity enhancing agent is lecithin.

17. The process of claim 13, wherein the enzyme activity enhancing agent is a combination of lecithin and at least one compound selected from the group consisting of chitin and chitosan.

18. The process of claim 17, wherein said chitin is a water-soluble chitin.

19. The process of claim 2, wherein the enzyme activity enhancing agent is used in an amount of at least 1% based on the weight of the lipase.

20. The process of claim 2, wherein the enzyme activity enhancing agent is used in an amount of at least 5% based on the weight of the lipase.

21. The process of claim 1 wherein the carrier is synthetic.

* * * * *